US011929169B2

(12) United States Patent
Miles et al.

(10) Patent No.: US 11,929,169 B2
(45) Date of Patent: Mar. 12, 2024

(54) PERSONALIZED SENSORY FEEDBACK

(71) Applicant: KYNDRYL, INC., New York, NY (US)

(72) Inventors: Caleb Miles, Columbia, MO (US); Shikhar Kwatra, San Jose, CA (US); Jennifer L. Szkatulski, Rochester, MI (US); Elio Andres Sanabria Echeverria, San Francisco, CA (US)

(73) Assignee: Kyndryl, Inc., New York, NY (US)

( * ) Notice: Subject to any disclaimer, the term of this patent is extended or adjusted under 35 U.S.C. 154(b) by 256 days.

(21) Appl. No.: 17/650,438

(22) Filed: Feb. 9, 2022

(65) Prior Publication Data

US 2023/0253105 A1 Aug. 10, 2023

(51) Int. Cl.
*G16H 40/67* (2018.01)
*G06N 20/00* (2019.01)

(52) U.S. Cl.
CPC ............. *G16H 40/67* (2018.01); *G06N 20/00* (2019.01)

(58) Field of Classification Search
CPC ............................... G16H 40/67; G06N 20/00
See application file for complete search history.

(56) References Cited

U.S. PATENT DOCUMENTS 9,483,771 B2 11/2016 Weerasinghe
9,588,588 B2 3/2017 Israr et al.
10,382,620 B1 * 8/2019 Allen ................ H04M 1/72463
10,469,769 B1 * 11/2019 Mukherjee .............. G06F 3/011
10,547,582 B1 * 1/2020 Kwatra ................... H04L 51/18
10,652,693 B2 * 5/2020 Jadav ................. G01C 21/3629
10,657,266 B2 * 5/2020 Hardee ................... G06F 21/60
10,667,081 B2 * 5/2020 Fox ....................... H04W 4/025
(Continued)

FOREIGN PATENT DOCUMENTS

CN 108021228 A 5/2018
KR 20130097801 A 9/2013
KR 20140138086 A 12/2014

OTHER PUBLICATIONS

Camarinha-Matos, Elsevier, 2021, pp. 1-268.*
(Continued)

*Primary Examiner* — Michael I Ezewoko
(74) *Attorney, Agent, or Firm* — CANTOR COLBURN LLP; Erik Swanson

(57) ABSTRACT

Personalizing sensory feedback based on user sensitivity analysis includes maintaining user-specific parameters for provision of sensory feedback to a user in extended reality. The user-specific parameters apply to specific contextual situations and dictate levels of sensory feedback to provide via stimulus device(s) in the specific contextual situations. Based on an ascertained contextual situation of the user interacting in a target extended reality environment, a set of sensory feedback level parameters is selected for provision of sensory feedback to the user in the target extended reality environment, and stimulus device(s) in the target extended reality environment is/are automatically controlled in the provision of the sensory feedback to the user based on one or more of the selected parameters. The automatically controlling includes electronically communicating with the stimulus device(s) to control at least one stimuli provided to the user by the stimulus device(s).

20 Claims, 5 Drawing Sheets

(56) References Cited

U.S. PATENT DOCUMENTS 10,708,421 B2 * 7/2020 Diriye .................. H04L 67/535
10,720,161 B2 * 7/2020 Castelli ............. H04N 21/4318
10,841,663 B2 * 11/2020 Kwatra ........... H04N 21/44218
10,885,755 B2 * 1/2021 Monge Nunez ....... G08B 25/14
10,891,843 B2 * 1/2021 Kwatra ................ G08B 21/043
10,891,954 B2 * 1/2021 Kwatra .................. G10L 15/30
10,902,735 B2 * 1/2021 Kozloski ................ G06N 3/006
10,924,417 B2 * 2/2021 Boss .................... H04L 67/535
10,937,127 B2 * 3/2021 Kwatra .................. G06T 3/403
10,938,762 B2 * 3/2021 Kwatra ................. H04L 51/216
10,938,985 B2 * 3/2021 Jaiswal ................ G06Q 30/016
10,942,369 B2 * 3/2021 Pinel ........................ A61B 3/11
10,943,588 B2 * 3/2021 Castelli .................. G10L 15/30
10,949,613 B2 * 3/2021 Freed .................... G06N 5/022
10,957,109 B2 * 3/2021 Bender .................. G06T 19/20
10,963,045 B2 * 3/2021 Weldemariam ...... A61B 5/6821
10,991,361 B2 * 4/2021 Kwatra ................. G10L 15/075
11,005,790 B2 * 5/2021 Lenchner .............. G06N 3/044
11,016,656 B1 * 5/2021 Covell ...................... G06T 7/20
11,042,230 B2 * 6/2021 Kochura ............. G06F 3/04883
11,055,119 B1 * 7/2021 Silverstein ............... G06N 3/08
11,068,969 B2 * 7/2021 Wilson .............. G06Q 30/0269
11,074,926 B1 * 7/2021 Baughman ............ G10L 21/003
11,082,283 B2 * 8/2021 Trim ...................... H04L 43/08
11,082,498 B2 * 8/2021 Kwatra ................ H04L 67/125
11,082,756 B2 * 8/2021 Rodriguez Bravo ....................... H04L 65/1069
11,093,118 B2 * 8/2021 Rodriguez Bravo ....................... H04L 67/535
11,122,198 B2 * 9/2021 Grant ........................ G06T 7/75
11,184,436 B2 * 11/2021 Kochura ................. H04L 67/10
11,184,736 B2 * 11/2021 Baughman ............. H04L 67/52
11,200,811 B2 * 12/2021 Kwatra ................. G09B 19/24
11,202,188 B1 * 12/2021 Baughman ............. G08B 7/066
11,205,422 B2 * 12/2021 Kwatra .................. G10L 25/24
11,211,072 B2 * 12/2021 Kwatra .................. G06F 3/167
11,223,800 B1 * 1/2022 Kwatra .................. H04N 7/157
11,224,801 B2 * 1/2022 Kwatra .................. A63F 13/98
11,301,223 B2 * 4/2022 Baughman ................ G06F 8/71
11,301,948 B2 * 4/2022 Weldemariam .......... G06N 3/04
11,303,683 B2 * 4/2022 Wilson ................. H04L 65/611
11,310,236 B2 * 4/2022 Rakshit .............. H04L 63/1433
11,310,624 B2 * 4/2022 Mukherjee-Roy ...... H04W 4/33
11,321,153 B1 * 5/2022 Kwatra ..................... G06F 7/26
11,321,487 B2 * 5/2022 Kwatra ................. H04W 12/63
11,321,758 B1 * 5/2022 Kwatra ............. G06Q 30/0639
11,327,747 B2 * 5/2022 Kwatra ..................... G06F 8/65
11,374,986 B1 * 6/2022 Silverstein ............ H04L 65/403
11,388,116 B2 * 7/2022 Kwatra ................. G06N 20/00
11,405,227 B2 * 8/2022 Kwatra ................. H04L 67/568
11,410,103 B2 * 8/2022 Kwatra ........... G06Q 10/06314
11,416,743 B2 * 8/2022 Baughman ............... G06N 3/08
11,423,583 B2 * 8/2022 Kwatra ................. G06F 18/251
11,423,775 B2 * 8/2022 Weldemariam ...... G08G 1/0129
11,429,996 B2 * 8/2022 Mazumder ......... G06Q 30/0631
11,442,457 B2 * 9/2022 Kwatra ................ G05D 1/0088
11,443,008 B2 * 9/2022 Weldemariam ....... G06F 40/106
11,445,042 B2 * 9/2022 Kwatra ................. G06N 20/00
11,452,940 B2 * 9/2022 Baughman .............. A63F 13/79
11,455,540 B2 * 9/2022 Baughman ............. G06N 5/022
11,481,401 B2 * 10/2022 Baughman .......... G06F 16/3329
11,481,460 B2 * 10/2022 Camus ................ G10L 15/1822
11,481,985 B1 * 10/2022 Sivaswamy ............ G16H 20/60
11,483,262 B2 * 10/2022 Kwatra ................ G06V 40/176
11,483,371 B2 * 10/2022 Jaiswal ................... H04L 67/02
11,488,240 B2 * 11/2022 Kochura ................. H04L 51/02
11,494,996 B2 * 11/2022 Baughman ............. G06N 20/00
11,500,660 B2 * 11/2022 Kwatra ................. G06N 5/022
11,501,059 B2 * 11/2022 Baysinger ............. G06F 40/174
11,501,530 B1 * 11/2022 Silverstein ............. G06V 40/18
11,503,526 B2 * 11/2022 Kwatra ................ H04B 17/318
11,507,193 B2 * 11/2022 Bradski ............... G06F 3/0346
11,513,822 B1 * 11/2022 Kwatra ................ G06F 3/0482
11,514,314 B2 * 11/2022 Baughman ........... G06V 10/774
11,514,507 B2 * 11/2022 Banipal ................... G06T 11/00
11,514,814 B2 * 11/2022 Wilson .................... G10L 15/22
11,520,601 B2 * 12/2022 Griffin .................... G06F 9/442
11,521,378 B2 * 12/2022 Grant ................... G08G 5/0021
11,525,684 B2 * 12/2022 Kozhaya .................. G06N 3/08
11,526,543 B2 * 12/2022 Keen ...................... G06N 3/045
11,526,612 B2 * 12/2022 Trim ..................... G06F 21/565
11,526,930 B2 * 12/2022 Yadav ................ G01C 21/3407
11,528,513 B2 * 12/2022 Hardee ............. G06Q 30/0251
11,537,875 B2 * 12/2022 Kozhaya .................. G06N 3/08
11,538,464 B2 * 12/2022 Baughman ............. G10L 25/03
11,546,181 B1 * 1/2023 Sivaswamy ........... H04W 4/021
11,550,827 B2 * 1/2023 Ravizza ............... G01C 21/387
11,552,966 B2 * 1/2023 Kwatra ................. G06F 16/248
11,556,335 B1 * 1/2023 Kwatra ..................... G06F 8/71
11,556,709 B2 * 1/2023 Trim ..................... G06F 40/253
11,556,720 B2 * 1/2023 Kwatra .................. G06N 20/00
11,558,335 B2 * 1/2023 Brooks Powell ...... G06N 3/088
11,562,029 B2 * 1/2023 Freed .................... G06F 16/906
11,568,087 B2 * 1/2023 Kinai ...................... G06F 9/547
11,568,612 B2 * 1/2023 Baughman ............... G09B 9/00
11,590,663 B2 * 2/2023 Silverstein ............. B25J 9/1664
11,606,221 B1 * 3/2023 Baughman .......... G06F 3/04845
11,615,163 B2 * 3/2023 Kwatra ............... G06F 16/9538 715/234
11,620,855 B2 * 4/2023 Kwatra ................. G06T 19/006 345/633
11,630,680 B2 * 4/2023 Kwatra .................. G06N 20/00 715/745
11,630,865 B2 * 4/2023 Kwatra ................. G06F 16/957 707/723
11,636,682 B2 * 4/2023 Kwatra .................. G06N 3/094 382/190
11,641,330 B2 * 5/2023 Flöther ................. H04L 51/216 704/9
11,645,498 B2 * 5/2023 Baughman ............... G06N 3/08 706/15
11,645,578 B2 * 5/2023 Kwatra ................... G06F 9/451 706/11
11,645,604 B2 * 5/2023 Kwatra ........... G06Q 10/06398 705/7.28
11,651,013 B2 * 5/2023 Banipal .................. G06N 20/00 707/722
11,657,227 B2 * 5/2023 Kwatra ................... G06F 40/30 704/9
11,657,558 B2 * 5/2023 Pandit .................... G06V 10/82 715/753
11,657,607 B2 * 5/2023 Kwatra .................. G06V 10/70 382/115
11,657,811 B2 * 5/2023 Kwatra ................... G06F 40/30 704/275
11,658,963 B2 * 5/2023 Silverstein .......... H04L 63/0853 726/9
11,663,480 B2 * 5/2023 Baughman ............. G06N 3/042 706/25
11,665,278 B2 * 5/2023 Tkaczyk ............... H04M 3/436 455/414.1
11,671,406 B2 * 6/2023 Kwatra .................. G16H 50/20 340/539.12
11,676,574 B2 * 6/2023 Rakshit .................... G06N 3/08 704/232
11,676,593 B2 * 6/2023 Kwatra ................. G10L 15/063 704/231
11,685,399 B2 * 6/2023 Kwatra .................. G06N 20/00 701/26
11,687,539 B2 * 6/2023 Baughman ............ G06F 16/355 707/748
11,687,633 B2 * 6/2023 Kwatra .................. G06N 5/022 704/232
11,687,806 B2 * 6/2023 Pandit ...................... G06N 5/04 706/12
11,705,125 B2 * 7/2023 Freed ...................... G10L 25/87 704/231
11,706,077 B2 * 7/2023 Trim ..................... H04L 9/3239 370/252
11,733,666 B2 * 8/2023 Kwatra .............. G05B 19/0421 700/28

(56) References Cited

U.S. PATENT DOCUMENTS 11,734,030 B2 * 8/2023 Kwatra .................. G06F 9/451 715/762
11,736,619 B2 * 8/2023 Kwatra .................. G16Y 40/30 370/259
11,741,177 B2 * 8/2023 Kwatra ............... G06F 16/9536 707/734
11,741,489 B2 * 8/2023 Karri ..................... G06T 11/00 705/14.25
11,748,636 B2 * 9/2023 Zhu ..................... G06Q 10/047 706/11
11,755,998 B2 * 9/2023 Malvankar ............. G06F 16/93 705/301
11,756,081 B2 * 9/2023 Griffin ................... G06F 3/013 705/14.67
11,770,585 B2 * 9/2023 Kwatra .................. G06V 20/41 725/10
11,779,811 B2 * 10/2023 Kwatra .............. A63B 24/0075 482/9
11,782,770 B2 * 10/2023 Baughman ........... G06F 9/5038 718/104
11,783,807 B2 * 10/2023 Kwatra .................. G06N 3/045 704/232
11,809,481 B2 * 11/2023 Banipal ................ G06F 16/483
11,822,896 B2 * 11/2023 Pandit .................... G06F 40/30
11,823,235 B1 * 11/2023 Fisher-Stawinski ........................ G06Q 30/0269
2012/0306632 A1 12/2012 Fleizach et al.
2014/0347176 A1 11/2014 Modarres et al.
2015/0324049 A1 11/2015 Kies et al.
2016/0378186 A1 12/2016 Kim
2017/0153702 A1 6/2017 Abrams et al.
2017/0168773 A1 6/2017 Keller et al.
2018/0308005 A1 * 10/2018 Banipal .................... G06N 3/04
2019/0065713 A1 * 2/2019 Hardee ............. G06Q 20/3224
2019/0080097 A1 * 3/2019 Hardee ............... G06F 21/6245
2019/0117142 A1 4/2019 Moskowitz
2019/0171988 A1 * 6/2019 Kwatra ........... G06Q 10/06314
2020/0036911 A1 * 1/2020 Mukherjee .............. B60R 1/002
2020/0151555 A1 * 5/2020 Kozhaya .................. G06N 3/08
2020/0169588 A1 * 5/2020 Wilson .................. H04L 65/611
2020/0249758 A1 8/2020 Khwaja et al.
2020/0315515 A1 * 10/2020 Kwatra .............. G08B 21/0476
2020/0372162 A1 * 11/2020 Kinai ..................... G06N 20/00
2020/0404002 A1 * 12/2020 Patel ....................... G06F 40/30
2020/0412682 A1 * 12/2020 Trim ...................... G06Q 10/10
2020/0413161 A1 * 12/2020 Rodriguez Bravo ....................... H04L 65/611
2021/0012440 A1 * 1/2021 Kwizera .............. G06Q 50/163
2021/0027643 A1 * 1/2021 Schume ................. G06N 5/022
2021/0055936 A1 * 2/2021 Griffin ................ H04W 52/028
2021/0056231 A1 * 2/2021 Kwatra ................. H04W 12/63
2021/0073060 A1 3/2021 Grant et al.
2021/0089869 A1 * 3/2021 Baughman .............. G10L 15/16
2021/0158143 A1 * 5/2021 Baughman ............... G06N 3/08
2021/0158406 A1 * 5/2021 Fox .................... G06Q 30/0282
2022/0004591 A1 * 1/2022 Camus .................... G06F 3/013
2022/0092604 A1 * 3/2022 Kwatra ................... H04W 4/80
2022/0092637 A1 * 3/2022 Trim .................. G06Q 30/0244
2022/0116203 A1 * 4/2022 Cannon .................. H04B 11/00
2022/0138473 A1 * 5/2022 Kwatra .................... G06N 3/04 382/190
2022/0138825 A1 * 5/2022 Kwatra ............... G06F 16/9538 705/7.31
2022/0138886 A1 * 5/2022 Rakshit .............. G06Q 30/0203 705/7.32
2022/0139245 A1 * 5/2022 Wilson ................ G06F 16/2457 434/362
2022/0147547 A1 * 5/2022 Kwatra ................. G06F 16/337
2022/0150189 A1 * 5/2022 Kwatra ................ G06V 40/176
2022/0164392 A1 * 5/2022 Kwatra ............... G06F 16/9535
2022/0164457 A1 * 5/2022 Baughman ............. G06N 3/088
2022/0166825 A1 * 5/2022 Jaiswal ................... H04L 67/02
2022/0171823 A1 * 6/2022 Kwatra ............... G06F 16/9538
2022/0172713 A1 * 6/2022 Kwatra ................... G10L 15/26
2022/0172714 A1 * 6/2022 Kwatra ................... G10L 15/16
2022/0198140 A1 * 6/2022 Trim .................. H04N 21/4394
2022/0261432 A1 * 8/2022 Banipal ............... G06F 16/4387
2022/0335041 A1 * 10/2022 Kwatra ................. G06F 16/248
2022/0335302 A1 * 10/2022 Banipal .................. G06N 3/088
2022/0392171 A1 * 12/2022 Baughman ........... G06T 19/006
2022/0405313 A1 * 12/2022 Banipal .................. G06N 3/047
2022/0405473 A1 * 12/2022 Diamanti ............... G06N 3/092
2022/0406304 A1 * 12/2022 Marzorati ................ G06N 3/09
2023/0046213 A1 * 2/2023 Karri ................. G06Q 30/0239
2023/0080387 A1 * 3/2023 Karri ...................... G06N 20/20 706/45
2023/0080417 A1 * 3/2023 Kwatra ................. G06F 18/214 706/12
2023/0081225 A1 * 3/2023 Fisher-Stawinski ... G16H 40/63 705/2
2023/0082635 A1 * 3/2023 Pandit ................... G06F 40/274 715/753
2023/0085012 A1 * 3/2023 Baughman ........... G06F 40/166 704/235
2023/0123240 A1 * 4/2023 Baughman ............ G06N 10/00 707/737
2023/0123399 A1 * 4/2023 Kwatra .............. G06Q 30/0609 705/26.35
2023/0144326 A1 * 5/2023 Sawarkar ........... H04N 21/4394 725/25
2023/0152115 A1 * 5/2023 Baughman ......... G01C 21/3697 701/436
2023/0153129 A1 * 5/2023 Kwatra .................... G09B 7/04 715/762
2023/0154609 A1 * 5/2023 Kwatra .................. G16H 10/60 705/2
2023/0171466 A1 * 6/2023 Kwatra ................... G06F 40/30 725/10
2023/0177612 A1 * 6/2023 Trim ...................... G06Q 40/08 705/4
2023/0178231 A1 * 6/2023 Baughman ............. G16H 40/63 705/2
2023/0182024 A1 * 6/2023 Baughman ............. A63F 13/75 705/44
2023/0186146 A1 * 6/2023 Baughman ............... G06N 7/01 706/12
2023/0188529 A1 * 6/2023 Kwatra ................. H04W 4/025 726/4
2023/0190061 A1 * 6/2023 Miles .................... A47L 9/2847 15/319
2023/0211560 A1 * 7/2023 Trim ........................ G06N 3/08 700/118
2023/0214411 A1 * 7/2023 Baughman ............ G06F 16/243 704/9
2023/0214422 A1 * 7/2023 Kwatra ................. G06F 16/783 707/736
2023/0214580 A1 * 7/2023 Baughman ............ G06F 40/263 704/8
2023/0214848 A1 * 7/2023 Sivaswamy .......... G06Q 30/018 705/317
2023/0281026 A1 * 9/2023 Kwatra .................. G06N 20/00 715/762
2023/0316215 A1 * 10/2023 Kwatra ............. G06Q 30/0208 705/330
2023/0367644 A1 * 11/2023 Marzorati ........... G06F 16/3344
2023/0368113 A1 * 11/2023 Sivaswamy ............. G10L 25/63

OTHER PUBLICATIONS

Towards artificial intelligence enabled 6G, Zhang, Elsevier, 2020, pp. 1-28.*

Anonymous, "Sentiment Driven Haptic Keyboard Effects," IP.com No. IPCOM000251602D, IP.com Electronic Publication Date: Nov. 15, 2017, 4 pgs.

(56) References Cited

OTHER PUBLICATIONS

Mell, Peter, et al., "The NIST Definition of Cloud Computing", NIST Special Publication 800-145, Sep. 2011, Gaithersburg, MD, 7 pgs.

* cited by examiner

PERSONALIZED SENSORY FEEDBACK

BACKGROUND

In many digital virtual reality (VR), augmented reality (AR), and mixed reality (MR) environments, sensory feedback is used to increase the immersion experience of the user. Sensory feedback refers to the provision of controlled sensory stimulus/stimuli to the user by one or more devices. Haptic, auditory, and visual feedback, corresponding to the senses of touch, hearing, and sight, respectfully, are most commonly used in VR/AR/MR systems, though gustatory (taste) and olfactory (smell) feedback is also possible. Sensory feedback may be unimodal, referring to provision of stimulus/stimuli along a single sense, or multimodal, referring to provision of stimuli along two or more senses. Different users have different sensory preferences and sensitivities, and therefore will respond differently to sensory sensations.

SUMMARY

Shortcomings of the prior art are overcome and additional advantages are provided through the provision of a computer-implemented method. The method maintains user-specific parameters for provision of sensory feedback to a user in extended reality. The user-specific parameters apply to specific contextual situations and dictate levels of sensory feedback to provide via stimulus device(s) in the specific contextual situations. The method also includes, based on an ascertained contextual situation of the user interacting in a target extended reality environment, selecting a set of sensory feedback level parameters for provision of sensory feedback to the user in the target extended reality environment. The method additionally includes automatically controlling, in the provision of the sensory feedback to the user in the target extended reality environment, at least one stimulus device in the target extended reality environment based on one or more of the selected parameters. The automatically controlling includes electronically communicating with the at least one stimulus device to control a stimulus or stimuli provided to the user by the at least one stimulus device.

Further, a computer system is provided that includes a memory and a processor in communication with the memory, wherein the computer system is configured to perform a method. The method maintains user-specific parameters for provision of sensory feedback to a user in extended reality. The user-specific parameters apply to specific contextual situations and dictate levels of sensory feedback to provide via stimulus device(s) in the specific contextual situations. The method also includes, based on an ascertained contextual situation of the user interacting in a target extended reality environment, selecting a set of sensory feedback level parameters for provision of sensory feedback to the user in the target extended reality environment. The method additionally includes automatically controlling, in the provision of the sensory feedback to the user in the target extended reality environment, at least one stimulus device in the target extended reality environment based on one or more of the selected parameters. The automatically controlling includes electronically communicating with the at least one stimulus device to control a stimulus or stimuli provided to the user by the at least one stimulus device.

Yet further, a computer program product including a computer readable storage medium readable by a processing circuit and storing instructions for execution by the processing circuit is provided for performing a method. The method maintains user-specific parameters for provision of sensory feedback to a user in extended reality. The user-specific parameters apply to specific contextual situations and dictate levels of sensory feedback to provide via stimulus device(s) in the specific contextual situations. The method also includes, based on an ascertained contextual situation of the user interacting in a target extended reality environment, selecting a set of sensory feedback level parameters for provision of sensory feedback to the user in the target extended reality environment. The method additionally includes automatically controlling, in the provision of the sensory feedback to the user in the target extended reality environment, at least one stimulus device in the target extended reality environment based on one or more of the selected parameters. The automatically controlling includes electronically communicating with the at least one stimulus device to control a stimulus or stimuli provided to the user by the at least one stimulus device.

Additional features and advantages are realized through the concepts described herein.

BRIEF DESCRIPTION OF THE DRAWINGS

Aspects described herein are particularly pointed out and distinctly claimed as examples in the claims at the conclusion of the specification. The foregoing and other objects, features, and advantages of the disclosure are apparent from the following detailed description taken in conjunction with the accompanying drawings in which:

DETAILED DESCRIPTION

Figure 1:
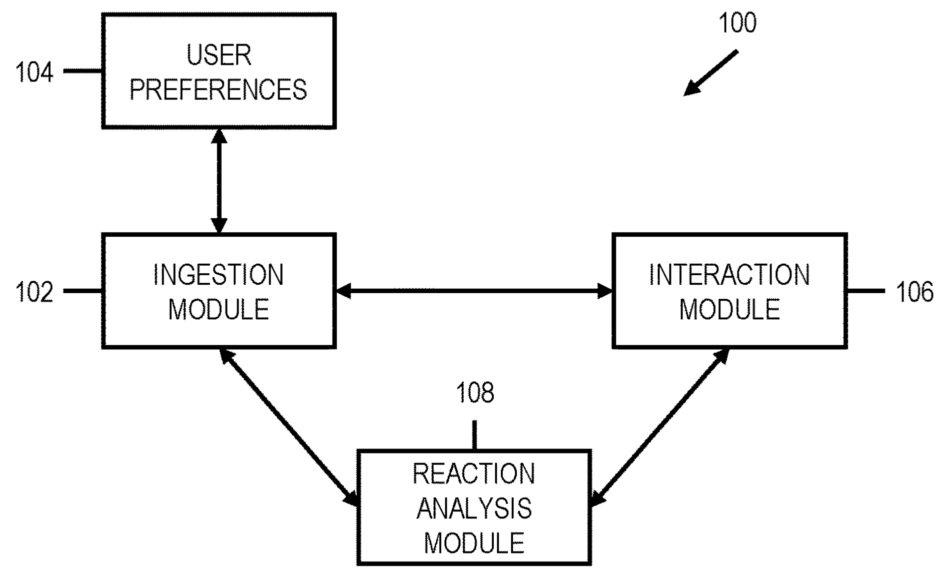
FIG. 1 depicts an example conceptual diagram of a system for personalizing sensory feedback based on sensitivity analysis, in accordance with aspects described herein.

Different users might respond differently to sensory sensations due to their specific sensory filtering capabilities and preferences. Described herein are approaches for tailoring and personalizing sensory feedback to specific users in order to cater to their specific preferences and needs. In accordance with some aspects, artificial intelligence (AI) models are trained using machine learning to learn over time, and for specific users, optimal settings for sensory feedback delivery given different contextual situations in which the user might be present. As an example, the optimal setting for auditory feedback to a given user when in a loud concert setting may be a significantly higher amplitude than when the user is in a much quieter library setting. Across users, the optimal settings for one user are likely to vary in comparison to the optimal settings for other users even in the same contextual setting. For instance, one user might be much harder of hearing than another user regardless of the environment, and therefore the optimal amplitude of auditory feedback may be higher in general for the one user than for the other user. An AI model can be trained based on feedback in the form of user-specified preferences in response to prompts as well observed reactions by the user to provided sensory feedback/stimuli, as explained herein.

Aspects apply to any AR, VR, or MR (collectively referred to herein as "extended reality" and "XR") environments in which sensory feedback is delivered to a user. By way of specific and non-limiting example, a gaming environment in which a user races a vehicle might deliver haptic feedback through a steering wheel or other controller that the user holds and auditory feedback in the form of screeching tires and engine noises through speakers (such as a headset or headphones). As another example, a virtual shopping experience might enable a user to experience a product based on sensory feedback to touch, sight, and/or smell. Additionally, aspects can be useful across individuals with varying levels of sensory feedback preferences and sensitivity differentials. Some users may be particularly prone to sensitive haptics or other sensory stimuli, and therefore aspects discussed herein may be useful in both adjusting, and assisting them to adjust, sensory feedback levels based on their specific preferences and sensitivities.

The dynamic personalization of sensory feedback controls in mixed-reality (virtual/augmented) environments is hereby provided based on identifying heuristics—specifically behavioral interactions (sensory feedback and user responses/behavior)—of the user over a time-series pattern, which correlates to the user's 'satisfaction' rating with delivered sensory feedback. These indicators are used to dictate whether and by how much to increase or decrease sensory feedback levels for that user. Tailoring the sensory feedback to a specific a user is nuanced and a 'slider bar solution' may not work. Instead, aspects take into account the user's preferences based on ongoing interactions and determine optimal sensory feedback parameters based on the user's interests/preferences and responses in order to personalize sensory feedback control as learned for specific users in accordance with the user's satisfaction rating. In examples, this is facilitated by a multi-agent reinforcement learning approach to personalize the sensory feedback based on optimizing a reward function proportional to the user's satisfaction rating. Supervised machine learning takes an indication of the user satisfaction with a delivered stimulus as example feedback for further training the AI model. In some aspects, unsupervised machine learning can be applied to new contextual situations in which the user has not yet been observed, and take, for instance, the identified heuristics of the user to determine the personalization of sensory feedback to that user in those new situations.

One embodiment of the implementation of aspects described herein is presented with reference to FIG. 1, depicting an example conceptual diagram of a system 100 for personalizing sensory feedback based on sensitivity analysis, in accordance with aspects described herein. The system could be implemented by hardware/software of one or more computer systems, and in a particular example is implemented at least in part by one or more backend or control computer systems (which might be of a cloud environment) and one or more sensor devices, for instance Internet-of-Things (IoT) devices configured to sense various types of user responses to stimuli. Some aspects of FIG. 1 and elsewhere herein are discussed relative, and with reference, to a specific user, but it should be understood that these aspects could be performed/repeated for a collection of related or unrelated users in order to personalize sensory feedback for each of the users of the collection.

An ingestion module 102 ingests and maintains knowledge about a user's preferences, personality, needs, etc. This information can be input or loaded into the system in any of various ways. For instance, the user can be prompted to input data into the system informing of these characteristics, including level(s) of sensory feedback that the user anticipates that he or she would desire or prefer in a presented contextual situation. A level of sensory feedback refers to the level (i.e. intensity, speed, magnitude, amplitude, duration or any other tailorable characteristic) of an individual stimulus. An anticipated preferred level of sensory feedback is the level that the user (or a system) anticipates that the desires or prefers. These could be solicited from the user through a prompt-response mechanism, such as questionnaires, surveys, or the like, and be maintained and stored as user preferences 104. Additionally, the collected user preferences may be relative to any number of varying environmental or contextual situations that are presented or proposed by the user and/or the system.

In some aspects, the system learns and updates such anticipated preferences over time to form and maintain a baseline as part of the user profiling. In this regard, a feedback mechanism might provide feedback relative to the user—either explicit feedback by the user or observed user reactions as feedback from the user—to help inform levels of stimuli that the user does or is expected/anticipated to prefer, and these levels might change over time. For instance, a user might initially indicate that the user is comfortable with haptic feedback of level 2 (on a scale of 1 to 10) in a given situation, such as playing a particular racing game using a particular single-handed controller, but the system might over time receive feedback that the user actually prefers a haptic feedback of level 5 in that contextual situation. Extending this, the system can also form anticipated preferences of the user that might change over time. For example, the system might apply what it has learned to anticipate that the user will prefer a mid-range (e.g. 5 of 10) level of haptic feedback when playing any type of game, and not just racing games, using that particular single-handed controller style, or that the user will prefer a lesser level of haptic feedback when the user is using a two-handed controller. In this manner, the feedback into the system to learn can apply both to contextual situations in which the user's reactions have been observed and also other contextual situations in which the user has not been observed previously or in which there is insufficient data to conclude what the user's sensory feedback preferences are for that particular contextual situation.

The ingestion module 102 can periodically or aperiodically request manual feedback from the user to confirm observed or provide anticipated (anticipated by the user or by the system) user-desired feedback levels. Thus, the ingestion module 102, or another component, could prompt the user to input desired actual or anticipated feedback level(s). Additionally, the system could prompt for such inputs, for instance by way of popup questions or verbal response requests, to confirm or adjust anticipated levels that the system learns and/or estimates about unknown contextual situations.

System 100 also includes machine-to-machine interaction module 106. Interaction module 106 leverages sensors to monitor user responses (also referred to herein as reactions) to sensory feedback provided to the user. The monitored responses are captured by the sensors as data that can be processed by the sensors themselves and/or by component(s)

in communication with the sensors, such as the interaction module 106 and/or a reaction analysis module 108. The machine-to-machine interactions can include those between the sensors, mechanisms, and other devices used within the system.

The sensors can be any appropriate devices to capture data about user reactions to provided sensory feedback. User reactions could be in any of various forms. Examples forms include, but are not limited to: sounds (e.g. spoken words, grunts, or any audible responses by the user), bodily movements (including movements of any body part(s), including facial expressions, body positions, and physical withdrawals from stimuli, as examples) and biological/physiological responses (such as changes in heartrate, body temperature, blood pressure, and perspiration as examples). Any form of reaction that can be sensed by sensor(s) is potentially useful.

In embodiments, the sensors are implemented by a combination of Internet-of-Things (IoT)-enabled sensors that gather data about the user before, during, and/or after sensory feedback is given to the user.

By way of specific example, cameras are one type of sensor that can be employed. Example cameras can capture images of the user and provide these for processing by the camera and/or other component(s). Example such processing includes executing a classifier (AI model) and determining a probability of various emotions being experienced by the user, ranked for instance on a varying scale such as 0-5, as a numerical feature vector in order to identify the user's emotional reactions. A specific example classifier for this is a Haar feature-based cascade classifier for object detection and facial recognition with emotion analysis. If a user emotion changes from a neutral or happy to pain immediately after sensory feedback is provided, then this suggests the sensory feedback was a negative experience and may be too intense.

As another example, specialized cameras such as thermal-imaging, night vision, and/or infrared cameras could be used, for instance to determine user temperatures over time and for feeding to a reinforcement learning module as part of reaction analysis.

Audio sensors can also be employed. In embodiments, microphone(s) installed in the environment in which the user is present can capture and process user's utterances. They could, for instance, recognize user speech patterns based on Mel frequency cepstral coefficients (MFCC) with a Gaussian mixture model (GMM) classifier. The microphone(s) could be installed in any device of the environment. Examples include devices with which the user physically interacts, such as the user's smartphone or a gaming controller, or other devices such as a monitoring controller or assist processor. The microphone(s) may be standalone devices that feed into a controller or other computer system.

In a specific example of audio processing, a backend/cloud-provided speech-to-text facility with conversation analysis is used to keep track of the user's vocal frequency variations and apply a convolutional neural network CNN on the voice frequency spectrogram of the user to classify reactions responsive to the sensory feedback. User frequency variations can inform of patterns in how a user expresses similar reactions to given stimuli levels. In this regard, artificial intelligence in the form of a machine learning model/AI model (sometimes referred to as a classifier) is used to learn, using the gathered audio of the user, the user's satisfaction level for different sensory stimuli.

Additionally, the audio processing can use natural language processing (NLP) to understand user expressions such as explicit expressions of a reaction (e.g. 'I did not like that') and exclamations ('Oh!'). If a user states out loud "that vibration was intense" or something semantically similar with a substantial enough frequency when provided a substantially similar stimulus level in substantially similar contextual situations, then this informs an environmental-behavioral feedback connection for that user, specifically that that level of stimulus (vibration) is too high for the user in that contextual situation.

A sentiment analysis model can be used as part of an NLP engine to detect sentiment in conjunction with speech frequency variations. Sentiment analysis can include/incorporate generic tone analysis as well. A model can be used to learn over time, using supervised learning, that a particular expression, content, or tone, when stated by the user, indicates a particular level of satisfaction (comfort or discomfort for instance) with a given sensory feedback level, for instance that the feedback was too intense or not intense enough. Agitated expressions regardless of whether the words used match each other can inform that a sensory feedback level is too intense. The sentiment analysis enables meaning to be derived from the content of the expression rather than just the frequency analysis of the sound that the user produced.

Accelerometer and other movement/position sensors can be used to collect data reflecting the user's orientation in space and user movement. These readings can be recorded to identify how the user physically reacts to provide sensory feedback, including the nature of movements (agitated, abrupt, casual, etc.) of the user when provided the sensory feedback and thereafter. The sensory data could be processed to detect, for instance, that the user physically withdrew from a stimulus, which is a notable reaction to reflect that the stimulus may have been too intense.

It is noted that various devices can deliver the stimuli, and the sensors could be part of or separate from the devices delivering the stimuli. A stimulus device is any device that provides a stimulus to the user as part of provided sensory feedback. Examples include actuators that move back and forth to deliver a vibration stimulus to the user, lights, monitors or other displays, wearable devices such as headsets, and speakers. Stimulus device as used herein can also encompass a controller or other computer system that controls or directs operation of such devices, for instance a computer system that electronically communicates with a stimulus device to control one or more stimuli provided to the user by that device. Examples electronic communications include communication to a speaker to direct audio emitted therefrom, communication to a display to provide graphical images, or communication to an actuator to vibrate.

The system can record and maintain records of sensory feedback, and variations thereof, provided to the user over time and additionally monitor the user's reactions thereto. Keeping track of feedback levels and user reactions can help track whether/how the user's responses change over time to given stimuli, for instance to identify situations where a user experiences a drift in sensitivity to stimuli by developing, for example, a tolerance/insensitivity to specific feedback levels over time.

System 100 of FIG. 1 also includes a reaction analysis module 108. In general, the reaction analysis module 108 analyzes the user's reactions (as sensed by the sensors of the interaction module 106) to the sensory feedback delivered. An aspect of this is monitoring against known environmental stimulation that may otherwise, if not taken into account, produce inaccurate results. The user's activity in a contextual situation may not be completely a result of sensory feedback. For instance, a user playing a video game might experience elevated body temperature and an agitated posture resulting from the user's activity of playing the game, and unrelated to any sensory feedback that the system 100 is providing to the user at that time. The experience of competition may be enough to generate an observable reaction of the user. The system 100 can observe the elevated body temperature and agitated posture of the user and understand that this is not a result of any sensory feedback being delivered by the system to the user. The system 100 can, for instance, align the observations of user reactions/responses to sensory feedback provided by the system 100 because the system 100 understands when it has directed stimulus device(s) to apply that feedback to the user.

In addition, the reaction analysis module 108 can transfer known user preferences of different types of feedback to other types of feedback. For instance, if a user prefers less intense vibration, the user may also prefer quieter audio feedback. These assumptions can be challenged and updated over time as the system 100 is used and the user is monitored. Assumptions that the system make as to user preferences can be challenged by providing sensory feedback to the user either in line or out of line with the assumed preferred level and monitoring the user's reactions to either confirm or refute what was expected. The system can expect that delivery of a more intense stimulus than what the system assumes to be the preferred level will produce a negative reaction from the user. If instead a positive or neutral reaction is observed, then the assumption by the system may be deemed incorrect and the system could adjust upward that anticipated preferred level of feedback.

A multi-agent reinforcement learning module implemented as part of reaction analysis module 108 or in/with another component of system 100 can be used to determine global optimal values of sensory feedback across contexts based on ongoing interaction of the user with the system. The reinforcement learning module utilizes a combination of states (S), transition probabilities for transitioning between those states based on Agent/user actions (A) as reactions to stimulus/stimuli, and environmental/contextual situations (E) for determining parameters of sensory feedback. For a given E, the user's action A may be a reaction (e.g. a verbal response or the user withdrawing away from a haptic feedback device for instance) to a stimulus at a probability of transition to a next state. The reinforcement learning module allows for reaction response determination and comparison.

As noted, there may be contextual situations that are not incorporated in the ingestion module 102, meaning it has not been previously observed with sufficient frequency how the user will react in the current contextual situation. Nonetheless, the system may be expected to have some assumption of the sensory feedback to deliver in the situation. While the ingestion module 102 can maintain preferences specific to each user, aspects can ingest preferences reflective of general populations to help inform assumptions about a user classified into those populations. For instance, people who work at concert venues may generally have a higher tolerance and/or preference for louder auditory feedback when interacting with a XR system on account that they experience loud environments more frequently than do other users. Similarly, an individual who works in a library may be less tolerant of abrupt loud noises than might other users who work in louder environments. There are many examples of 'populations' than can be classified together in terms of their preferences for various sensory feedback levels. Accordingly, the system can build/use templates or baselines in terms of anticipated preferred sensory feedback level parameters for various populations and can classify a given user into one or more of those populations. Such templates can be used as a baseline for a given user and adjusted over time as more feedback is ingested as to user preferences and reactions to provided sensory feedback. The user's preferred sensory feedback levels can thereby be based initially on a baseline or template informed by properties or attributes of the user and then tailored based on how the user responds to sensory feedback provided in varying specific situations. Accordingly, based on clustering of different use cases for different users/classes of users via profiling (similarity analysis based on heuristics done using cosine similarity of various parameters, for instance) a multi-agent reinforcement learning model can be incorporated and used by the system for informing anticipated preferred sensory feedback levels to use in these clustered use cases.

By way of specific example of the multi-agent reinforcement learning model, at each time step t the agent (user) takes an action (At). The system and the stimulus is updated given the action At of the user, the user emits observation Ot captured via the multi-modal sensory input sensing system as explained above, and reward Rt is allocated based on the given state St. Over time, this updating is based on the feedback mechanism (see return from 208 to 206 in FIG. 2 below), for instance observed user reactions and/or prompts to the user to express the user's feelings about a stimulus/stimuli. The 'reward' is the change of stimulus (removal or delivery, and at a specified level). In this manner, there is some current state in which the user is currently and there is an observation by the system of a user action followed by a determined 'reward', i.e. stimulus/stimuli or negation of a stimulus/stimuli for instance. The determined reward is a determination as to validation of the stimulus/stimuli or adjustment of the stimulus/stimuli (positive or negative). A reward function used may be proportional to the satisfaction rating or feedback exhibited by the agent/user, as follows: Reward function=K*function (satisfaction rating)=K*function (alpha*sentiment+beta*emotion_probability+gamma*(accelerometer+gesture)+kappa*Conversational insights).

K, alpha, beta, gamma, and kappa are coefficients/variables that can be determined and/or learned based on feedback over time. Sentiment, emotion_probability, accelerometer, gesture, and conversational insights are measurements/markers of user reactions as explained above relative to the interaction module 106. Over time, and based on the reward gradient, the system will reach a global optimal value based on interaction of the user with the system for a given contextual situation, i.e. the presented environment. In other words, the model will learn the parameters for optimal sensory feedback level delivery (which includes for instance stimulus levels) for a given user and for a given a set of environmental/contextual parameters. In different environment/contextual situations, the parameters of sensory feedback level to provide to the user may vary.

Figure 2:
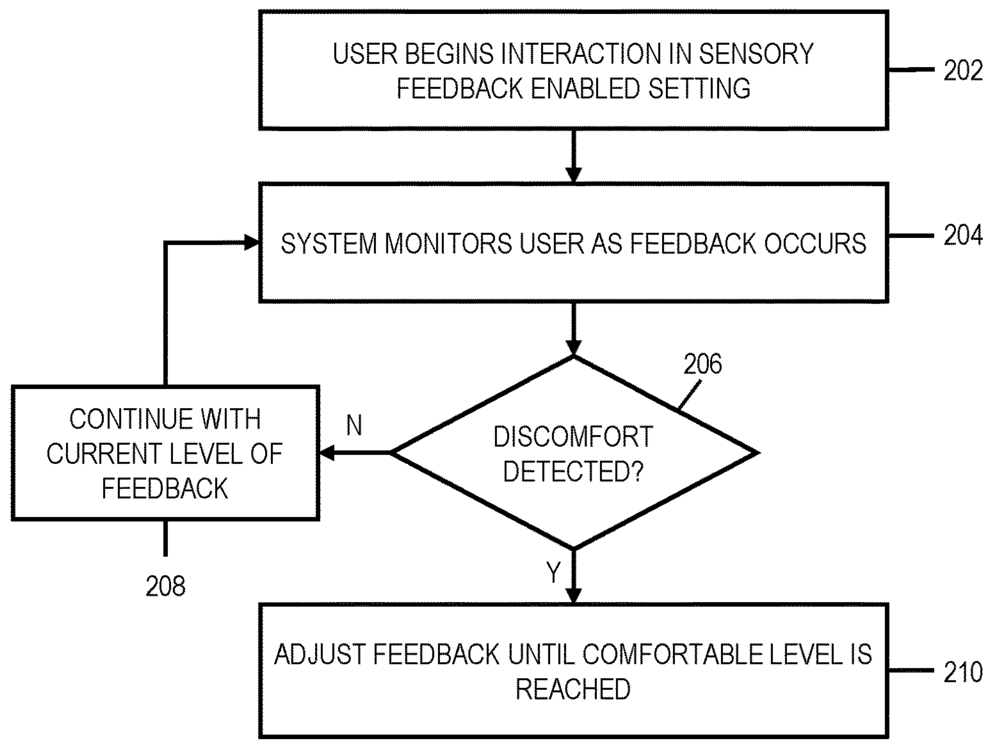
FIG. 2 depicts an example process used in multi-agent reinforcement learning in accordance with aspects described herein.

FIG. 2 depicts an example process used in multi-agent reinforcement learning in accordance with aspects described herein. Aspects of the process may be performed by software executing on one or more computer systems. The process picks up with the user beginning to interact (202) in a sensory feedback enabled setting/environment/contextual situation. As an example, the user begins engaging with an XR system/environment incorporating stimulus devices to provide sensory feedback to the user. After providing sensory feedback, which includes one or more stimuli each delivered at respective parameters for intensity, level, or the like, the system monitors (204) the user reactions as the sensory feedback is provided. The process then inquires (206) whether discomfort is detected in the user during provision of the sensory feedback. If not (206, N), the process continues with the current level of sensory feedback and returns to 204. This refers to maintaining the current parameters of preferred or anticipated preferred sensory feedback level(s) for that user in that current contextual situation. For instance, if haptic feedback is provided at a level of 5 each time the user swings a golf club in a virtual reality golf game and no discomfort is detected for that feedback level, the system will continue with that level of haptic feedback when the user swings the golf club. The process of FIG. 2 can loop through 204, 206 over time as the current level of feedback remains appropriate.

Additionally or alternatively, as noted above the system can periodically or aperiodically challenge known or assumed anticipated preferred feedback levels as one form of check on the accuracy of the system. For instance, the system could intentionally provide a feedback level above or below the current level of feedback (at which the user apparently does not feel discomfort) and learn based on the user's reaction, as observed using the sensors and/or as answered after a prompt to the user, after delivery of the deviant feedback level whether the current level remains appropriate. If the user expresses dissatisfaction at a lower feedback level than the current level, this may be taken as reinforcement that the current level is optimal. If the user expresses satisfaction (or fails to express dissatisfaction) after being provided a higher feedback level than the current level that the system thinks is optimal, then the system might gradually increase the current 'optimal' feedback level toward the higher feedback level and monitor user reaction based on that.

Returning to FIG. 2, if discomfort is detected at 206 (206, Y), the process adjusts (210) the feedback level until the optimal/comfortable level is reached. In a specific example, this involves gradual or drastic adjustment followed by additional monitoring/observation (204) and inquiry (206) about discomfort after the change.

In accordance with aspects of FIG. 2, feedback to the system in the form of user reactions to sensory feedback/stimulation is used to tailor parameters of such sensory feedback in order to determine optimal levels for the user in a given situation. The process of FIG. 2 can be performed continually over time and may be instantiated separately whenever there is a change in the contextual situation or account for such changes. For instance, there might be an environmental change at some point while looping over 204, 206 and 208, or user preference might change during that time. In this manner, environmental changes in the environment might present a different contextual situation (rising temperature, change of season, increase in ambient noise, etc.). The user might relocate to another environment or change a game being played on the XR system. These are just examples of the infinite ways the contextual situation might change.

Provided thereby is dynamic personalization of haptic and other sensory feedback controls in extended reality environments based on identifying user's heuristics over a time-series pattern which correlates to the user's satisfaction rating. A multi-agent reinforcement learning model approach is leveraged to personalize the sensory feedback, based on optimizing a reward function, proportional to the user satisfaction rating in an iterative fashion to continue improving the user experience and learn from other multi-variate data being continuously ingested. New reactions are continuously observed and analyzed, as a stream of information into the multi-agent reinforcement learning framework, to train, in real time and using this feedback, the model to adjust satisfaction accordingly by tweaking the sensor feedback levels.

Aspects can be used in situations involving users with different sensory sensitivities such that struggles with sensory overload might otherwise result. A system to learn the preferred sensory intensities specifically catered to individual users would allow them to experience the sensory feedback without unpleasant sensory overload at intensities that might otherwise be set as a default. Similarly, these aspects can be leveraged to enhance user experience by adjusting levels in situations where levels are too intense or too weak such that it inhibits the user experience. Additionally, aspects provide for customized sensory input based upon user response; messages from sender A show more significance to user than Sender B and sensory feedback responds accordingly. For instance, users with heightened sensitivity to auditory or tactile feedback mechanisms (as examples) may experience diminished feedback in accordance with user preferences and sender priorities. Thus, elements of greater significance result in differentiated sensitivity action.

Figure 3:
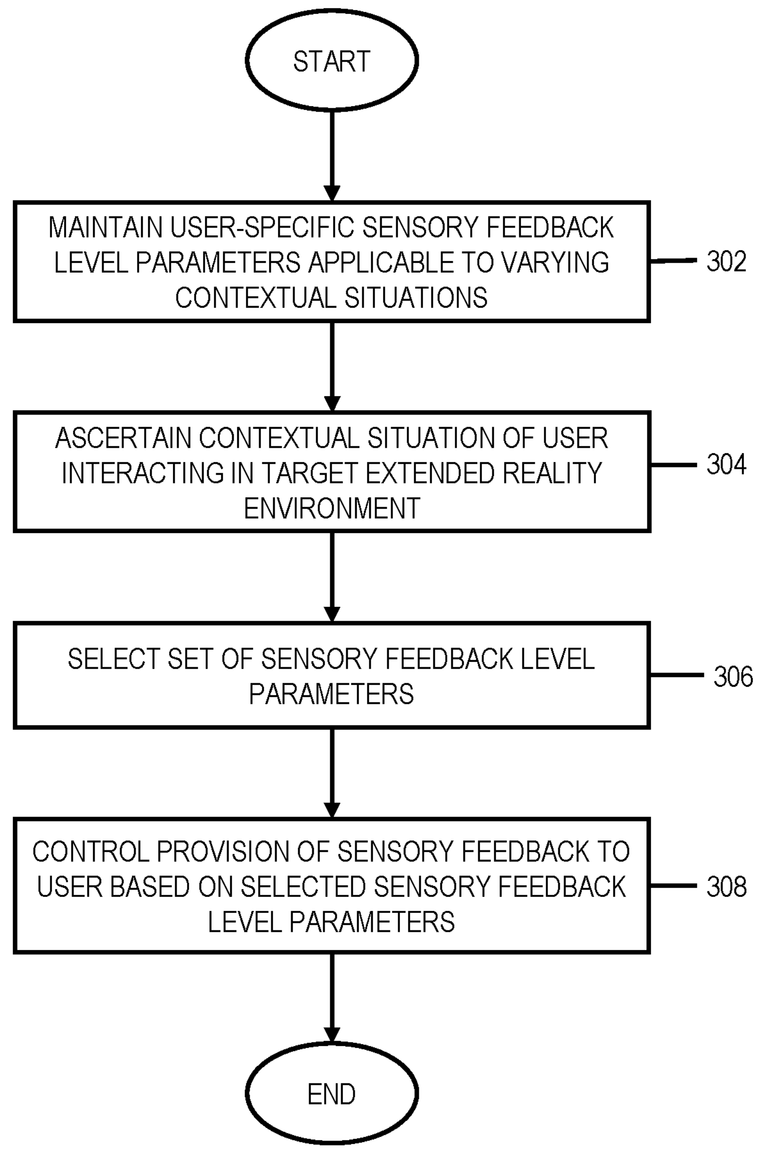
FIG. 3 depicts an example process for personalizing sensory feedback based on user sensitivity analysis, in accordance with aspects described herein.

FIG. 3 depicts an example process for personalizing sensory feedback based on user sensitivity analysis, in accordance with aspects described herein. In some examples, the process is performed by one or more computer systems, such as those described herein. The process includes maintaining (302) user-specific parameters for provision of sensory feedback to a user in extended reality. The user-specific parameters apply to specific contextual situations and dictate levels of sensory feedback to provide via one or more stimulus devices in the specific contextual situations. Thus, in examples, there are correlations between different sets of parameters and different contextual situations for which those parameters are to be used in providing sensory feedback to that user. The parameters are for controlling stimuli delivery in extended reality environments, which include, as examples augmented reality, virtual reality, and mixed-reality environments including different sensors and stimulus devices thereof. The particular extended reality environment is just one component of a contextual situation; any parameter or characteristics associated with a user's engagement with an XR environment could inform the contextual situation, including environmental variables such as ambient noise, weather, and the particular sensory feedback devices involved, emotional, mental, biological, medical or physical characteristics of the user at that time, the particularities of what the user is doing while interacting with the XR environment, and any other contextual parameters.

In embodiments, maintaining the user-specific parameters includes maintaining unique sets of sensory feedback level parameters correlating to different contextual situations in which user reactions have been previously observed. A given set of parameters can apply to a group of contextual situations that are considered sufficiently similar to each other such that those parameters are appropriate for all such situations of that group. For instance, the contextual situation of a loud concert venue might be sufficiently similar to that of a loud sporting event such that the set of parameters to use in providing sensory feedback to a user in both such situations is the same.

In embodiments, the maintaining includes using feedback from the user. The feedback could be provided in the form of observed user reactions to provided stimuli in one or more extended reality environments and/or user responses to prompts (such as questions about the user's level of comfort with provided stimuli), as examples. The feedback may be used as input to train an AI model, such as a Multi-Agent Reinforcement Learning (MARL) AI model to identify the user-specific parameters applying to the specific contextual situations.

The process of FIG. 3 continues by ascertaining (304) a contextual situation of the user interacting in a target extended reality environment and selecting (306) a set of sensory feedback level parameters for provision of sensory feedback to the user in the target extended reality environment based on such ascertaining. In examples in which a MARL AI model is utilized, the selecting can include applying the MARL AI model to features of the ascertained contextual situation and obtain as an output of the model a classification of the set of sensory feedback level parameters to select.

In embodiments, the selecting (306) includes comparing the ascertained contextual situation to one or more of the different contextual situations and determining based on the comparing whether the ascertained contextual situation corresponds to a contextual situation of the different contextual situations. The selecting (306) of the selected set of sensory feedback level parameters can be based on this determining. As one example, in situations when the determining determines that the ascertained contextual situation corresponds to a contextual situation of the different contextual situations, the selected set of sensory feedback level parameters can be the unique set of sensory feedback level parameters correlating to the contextual situation to which the ascertained contextual situation corresponds. By 'corresponds' is meant that the ascertained contextual situation is either an exact match to the contextual situation of the different contextual situation or is a substantially/sufficiently similar to the contextual situation of the different contextual situation. Similarity in this context can refer to a threshold-based determination of similarity, which might employ a trained AI model trained over time to learn contextual situations that correspond to each other.

In embodiments, maintaining the user-specific parameters includes maintaining one or more sets of anticipated preferred sensory feedback levels for the user. These may be sensory feedback levels that have not yet been confirmed through sufficient (or even any) observations of the user in corresponding contextual situations but that are anticipated or suggested based on any of various considerations such as user input or grouping the user into one or more populations. In this regard, the determination of whether the ascertained contextual situation corresponds to a contextual situation of the different contextual situations can determine that the ascertained contextual situation does not correspond to any contextual situation of the different contextual situations, in which case the selected set of sensory feedback level parameters can be a set of the one or more aforementioned anticipated preferred sensory feedback level parameters for the user.

In a particular example, the selected set of anticipated preferred sensory feedback level parameters for the user is based on a template set of sensory feedback level parameters built based on a population of users in which the user is classified. Such a template can be built and trained on a group of other users that are similarly situated to the user for which the parameters are being selected. That user might fit into one or more groups of users and there may be a corresponding one or more parameter templates available that were built and trained on such groups of users. The template approach may provide more accurate parameters for the particular user than, say, a default set of parameters that might otherwise apply in a contextual situation that this user has not previously been in.

Continuing with FIG. 3, the process automatically controls (308), in the provision of the sensory feedback to the user in the target extended reality environment, at least one stimulus device in the target extended reality environment based on one or more of the selected parameters. This automatically controlling includes electronically communicating with the at least one stimulus device to control one or more stimuli provided to the user by the at least one stimulus device. As a specific example, the parameters inform the level(s) of sensory feedback that a controller or other computer system performing the automatic controlling is to dictate that stimulus device(s) provide to the user as part of the extended reality experience in the target extended reality environment.

Although various examples are provided, variations are possible without departing from a spirit of the claimed aspects.

Figure 6:
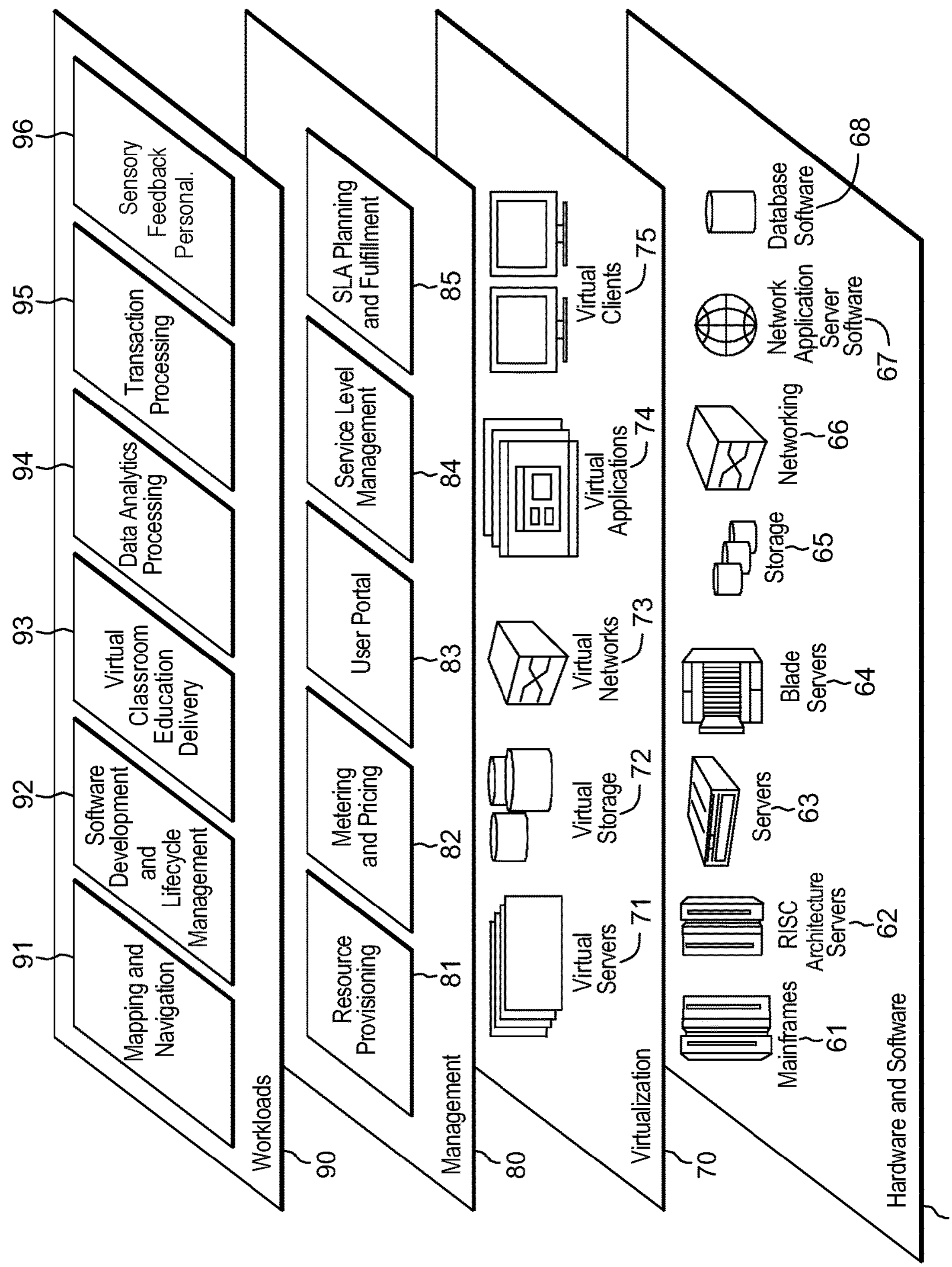
FIG. 6 depicts abstraction model layers according to an embodiment of the present invention.

Processes described herein may be performed singly or collectively by one or more computer systems and/or associated devices described herein such as sensors, controllers, or the like. FIG. 6 depicts one example of such a computer system and associated devices to incorporate and/or use aspects described herein. A computer system may also be referred to herein as a data processing device/system, computing device/system/node, or simply a computer. The computer system may be based on one or more of various system architectures and/or instruction set architectures, such as those offered by Intel Corporation (Santa Clara, California, USA) or ARM Holdings plc (Cambridge, England, United Kingdom), as examples.

Figure 4:
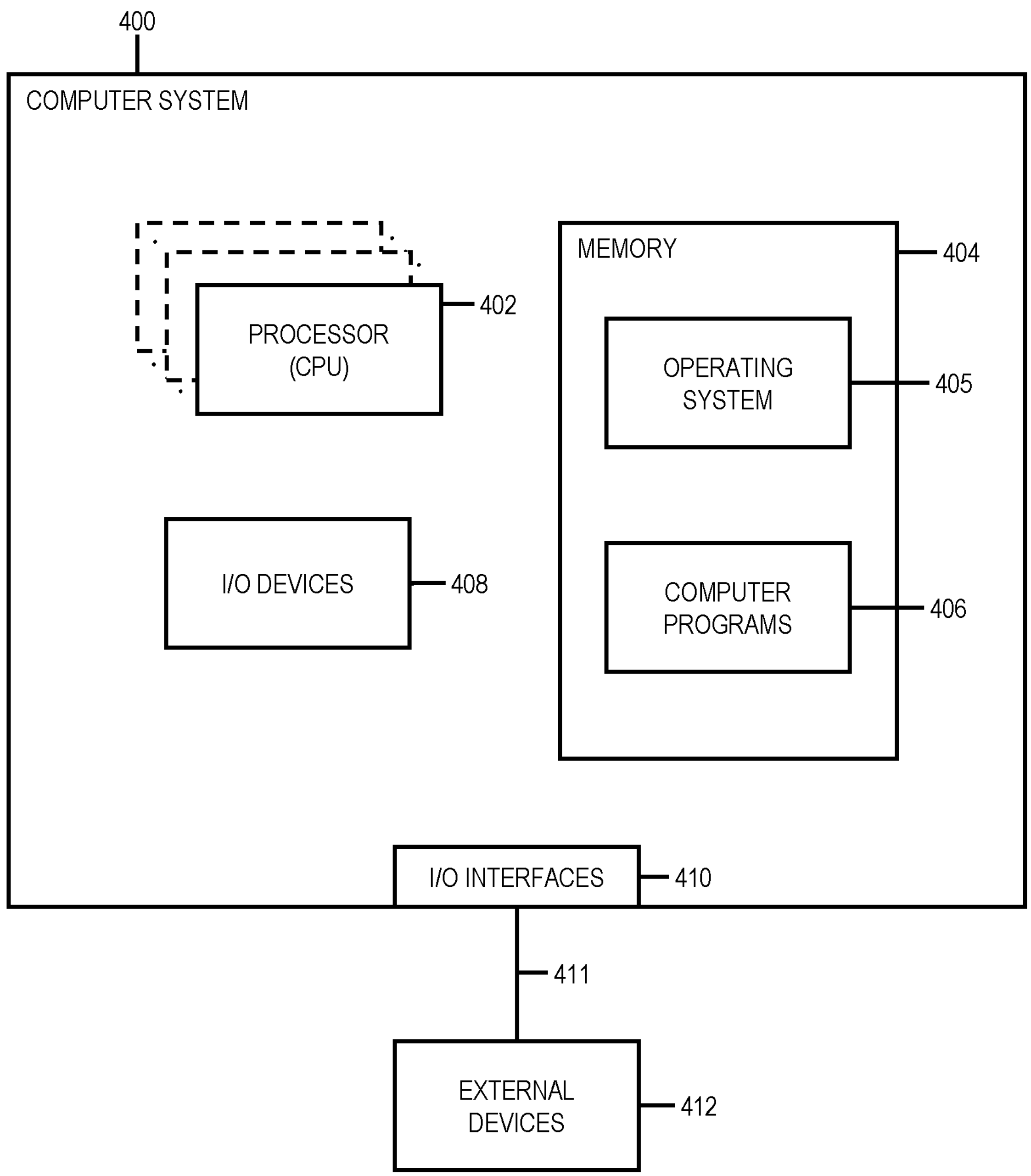
FIG. 4 depicts one example of a computer system and associated devices to incorporate and/or use aspects described herein.

FIG. 4 shows a computer system 400 in communication with external device(s) 412. Computer system 400 includes one or more processor(s) 402, for instance central processing unit(s) (CPUs). A processor can include functional components used in the execution of instructions, such as functional components to fetch program instructions from locations such as cache or main memory, decode program instructions, and execute program instructions, access memory for instruction execution, and write results of the executed instructions. A processor 402 can also include register(s) to be used by one or more of the functional components. Computer system 400 also includes memory 404, input/output (I/O) devices 408, and I/O interfaces 410, which may be coupled to processor(s) 402 and each other via one or more buses and/or other connections. Bus connections represent one or more of any of several types of bus structures, including a memory bus or memory controller, a peripheral bus, an accelerated graphics port, and a processor or local bus using any of a variety of bus architectures. By way of example, and not limitation, such architectures include the Industry Standard Architecture (ISA), the Micro Channel Architecture (MCA), the Enhanced ISA (EISA), the Video Electronics Standards Association (VESA) local bus, and the Peripheral Component Interconnect (PCI).

Memory 404 can be or include main or system memory (e.g. Random Access Memory) used in the execution of program instructions, storage device(s) such as hard drive(s), flash media, or optical media as examples, and/or cache memory, as examples. Memory 404 can include, for instance, a cache, such as a shared cache, which may be coupled to local caches (examples include L1 cache, L2 cache, etc.) of processor(s) 402. Additionally, memory 404 may be or include at least one computer program product having a set (e.g., at least one) of program modules, instructions, code or the like that is/are configured to carry out functions of embodiments described herein when executed by one or more processors.

Memory 404 can store an operating system 405 and other computer programs 406, such as one or more computer programs/applications that execute to perform aspects described herein. Specifically, programs/applications can include computer readable program instructions that may be configured to carry out functions of embodiments of aspects described herein.

Examples of I/O devices 408 include but are not limited to microphones, speakers, Global Positioning System (GPS) devices, cameras, lights, accelerometers, gyroscopes, magnetometers, sensor devices such as those configured to sense light, proximity, heart rate, body and/or ambient temperature, blood pressure, and/or skin resistance, and activity monitors. Additionally, I/O devices 408 could be or include any sensor devices and/or stimulus devices described herein. An I/O device may be incorporated into the computer system as shown, though in some embodiments an I/O device may be regarded as an external device (412) coupled to the computer system through one or more I/O interfaces 410.

Computer system 400 may communicate with one or more external devices 412 via one or more I/O interfaces 410. Example external devices include a keyboard, a pointing device, a display, and/or any other devices that enable a user to interact with computer system 400. Other example external devices include any device that enables computer system 400 to communicate with one or more other computing systems or peripheral devices such as a printer. A network interface/adapter is an example I/O interface that enables computer system 400 to communicate with one or more networks, such as a local area network (LAN), a general wide area network (WAN), and/or a public network (e.g., the Internet), providing communication with other computing devices or systems, storage devices, or the like. Ethernet-based (such as Wi-Fi) interfaces and Bluetooth® adapters are just examples of the currently available types of network adapters used in computer systems (BLUETOOTH is a registered trademark of Bluetooth SIG, Inc., Kirkland, Washington, U.S.A.).

The communication between I/O interfaces 410 and external devices 412 can occur across wired and/or wireless communications link(s) 411, such as Ethernet-based wired or wireless connections. Example wireless connections include cellular, Wi-Fi, Bluetooth®, proximity-based, near-field, or other types of wireless connections. More generally, communications link(s) 411 may be any appropriate wireless and/or wired communication link(s) for communicating data.

Particular external device(s) 412 may include one or more data storage devices, which may store one or more programs, one or more computer readable program instructions, and/or data, etc. Computer system 400 may include and/or be coupled to and in communication with (e.g. as an external device of the computer system) removable/non-removable, volatile/non-volatile computer system storage media. For example, it may include and/or be coupled to a non-removable, non-volatile magnetic media (typically called a "hard drive"), a magnetic disk drive for reading from and writing to a removable, non-volatile magnetic disk (e.g., a "floppy disk"), and/or an optical disk drive for reading from or writing to a removable, non-volatile optical disk, such as a CD-ROM, DVD-ROM or other optical media.

Computer system 400 may be operational with numerous other general purpose or special purpose computing system environments or configurations. Computer system 400 may take any of various forms, well-known examples of which include, but are not limited to, personal computer (PC) system(s), server computer system(s), such as messaging server(s), thin client(s), thick client(s), workstation(s), laptop(s), handheld device(s), mobile device(s)/computer(s) such as smartphone(s), tablet(s), and wearable device(s), multiprocessor system(s), microprocessor-based system(s), telephony device(s), network appliance(s) (such as edge appliance(s)), virtualization device(s), storage controller(s), set top box(es), programmable consumer electronic(s), network PC(s), minicomputer system(s), mainframe computer system(s), and distributed cloud computing environment(s) that include any of the above systems or devices, and the like.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 5:
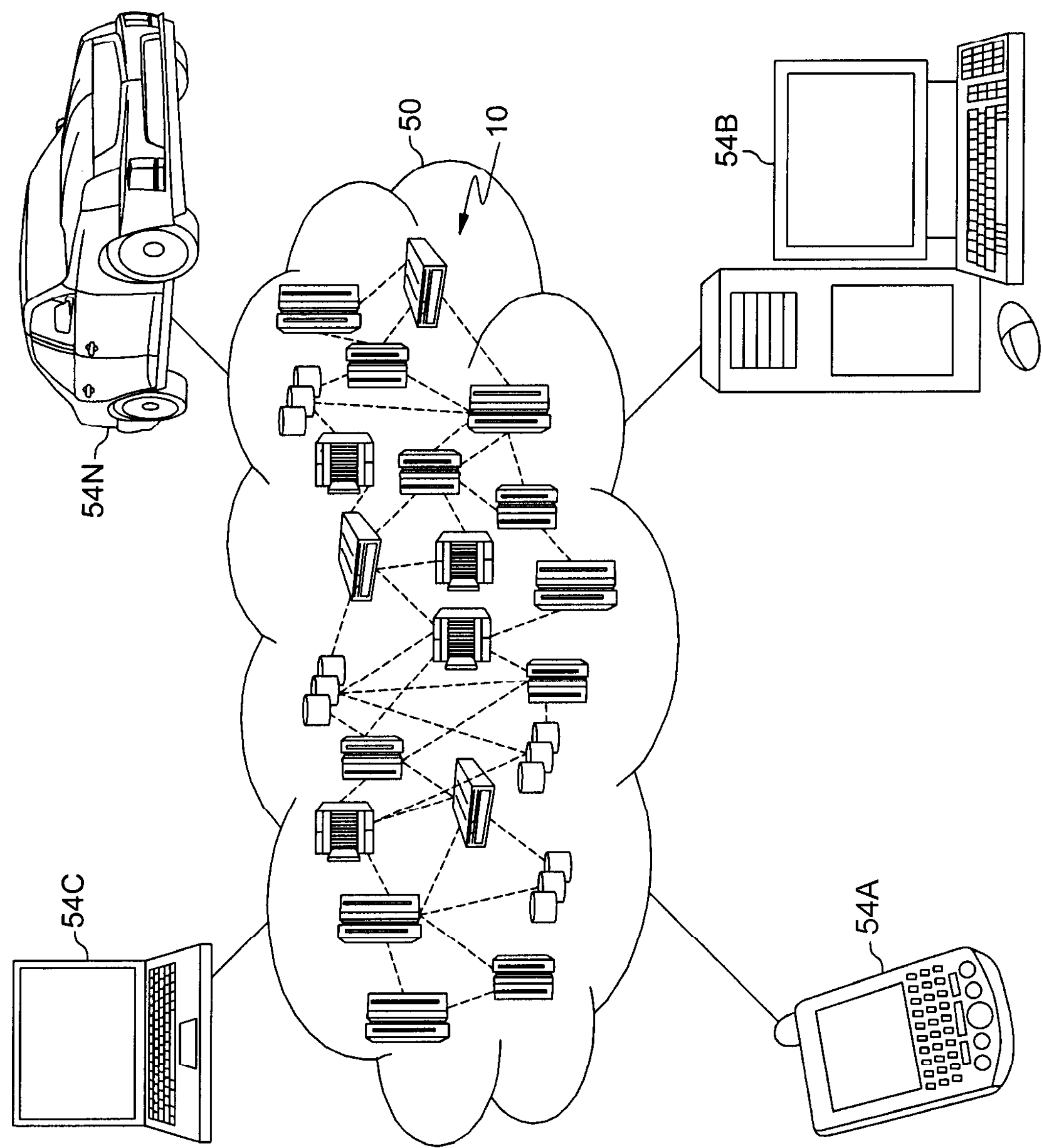
FIG. 5 depicts a cloud computing environment according to an embodiment of the present invention.

Referring now to FIG. 5, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 10 and cloud computing environment 50 can communicate with any type of computerized device over any type of network and/or network addressable connection (e.g., using a web browser).

Referring now to FIG. 6, a set of functional abstraction layers provided by cloud computing environment 50 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and sensory feedback personalization 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In addition to the above, one or more aspects may be provided, offered, deployed, managed, serviced, etc. by a service provider who offers management of customer environments. For instance, the service provider can create, maintain, support, etc. computer code and/or a computer infrastructure that performs one or more aspects for one or more customers. In return, the service provider may receive payment from the customer under a subscription and/or fee agreement, as examples. Additionally or alternatively, the service provider may receive payment from the sale of advertising content to one or more third parties.

In one aspect, an application may be deployed for performing one or more embodiments. As one example, the deploying of an application comprises providing computer infrastructure operable to perform one or more embodiments.

As a further aspect, a computing infrastructure may be deployed comprising integrating computer readable code into a computing system, in which the code in combination with the computing system is capable of performing one or more embodiments.

As yet a further aspect, a process for integrating computing infrastructure comprising integrating computer readable code into a computer system may be provided. The computer system comprises a computer readable medium, in which the computer medium comprises one or more embodiments. The code in combination with the computer system is capable of performing one or more embodiments.

Although various embodiments are described above, these are only examples.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the claims below, if any, are intended to include any structure, material, or act for performing the function in combination with other claimed elements as specifically claimed. The description of one or more embodiments has been presented for purposes of illustration and description, but is not intended to be exhaustive or limited to in the form disclosed. Many modifications and variations will be apparent to those of ordinary skill in the art. The embodiment was chosen and described in order to best explain various aspects and the practical application, and to enable others of ordinary skill in the art to understand various embodiments with various modifications as are suited to the particular use contemplated.

What is claimed is:

1. A computer-implemented method comprising:

maintaining user-specific parameters for provision of sensory feedback to a user in extended reality, the user-specific parameters applying to specific contextual situations and dictating levels of sensory feedback to provide via one or more stimulus devices in the specific contextual situations, wherein the maintaining comprises using feedback captured from user responses to generated prompts to the user, as input to train a Multi-Agent Reinforcement Learning (MARL) artificial intelligence (AI) model to identify the user-specific parameters applying to the specific contextual situations;

based on an ascertained contextual situation of the user interacting in a target extended reality environment, selecting a set of sensory feedback level parameters for provision of sensory feedback to the user in the target extended reality environment, wherein the sensory feedback is in response to generating a plurality of questions about a user's comfort level, wherein the selecting comprises applying the MARL AI model to features of the ascertained contextual situation and obtaining as an output of the MARL AI model a classification of the set of sensory feedback level parameters, wherein the sensory feedback is personalized to the user based on employing a reward function parametrized on factors including sentiment data and accelerometer data, wherein the sentiment data is detected by an NLP engine and the accelerometer data including the user's movement and orientation in space is captured with an accelerometer;

training the MARL AI model in real-time using the sensory feedback from a user apparatus producing the accelerometer data, the sensory feedback being received from the user in real-time including new reactions, iteratively adjusting the set of sensory feedback level parameters of the MARL AI model based on the sensory feedback; and automatically controlling, in the provision of the sensory feedback to the user in the target extended reality environment, at least one stimulus device in the target extended reality environment based on one or more of the selected parameters, the automatically controlling comprising electronically communicating with the at least one stimulus device to control one or more stimuli provided to the user by the at least one stimulus device.

2. The method of claim 1, wherein the maintaining the user-specific parameters comprises maintaining unique sets of sensory feedback level parameters correlating to different contextual situations in which user reactions have been previously observed.

3. The method of claim 2, wherein the selecting comprises comparing the ascertained contextual situation to one or more of the different contextual situations and determining based on the comparing whether the ascertained contextual situation corresponds to a contextual situation of the different contextual situations, and wherein the selecting of the selected set of sensory feedback level parameters is based on the determining.

4. The method of claim 3, wherein the determining determines that the ascertained contextual situation corresponds to a contextual situation of the different contextual situations, and wherein the selected set of sensory feedback level parameters is the unique set of sensory feedback level parameters correlating to the contextual situation to which the ascertained contextual situation corresponds.

5. The method of claim 3, wherein maintaining the user-specific parameters comprises maintaining one or more sets of anticipated preferred sensory feedback levels for the user, wherein the determining determines that the ascertained contextual situation does not correspond to any contextual situation of the different contextual situations, and wherein the selected set of sensory feedback level parameters is a set of anticipated preferred sensory feedback level parameters of the one or more sets of anticipated preferred sensory feedback levels for the user.

6. The method of claim 5, wherein the selected set of anticipated preferred sensory feedback level parameters for the user is based on a template set of sensory feedback level parameters built based on a population of users in which the user is classified.

7. The method of claim 1, wherein the maintaining further comprises using feedback employing observed user reactions to provided stimuli in one or more extended reality environments.

8. The method of claim 1, wherein different specific contextual situations comprises different extended reality environments comprising different sensors and stimulus devices thereof.

9. The method of claim 1, wherein the target extended reality environment comprises at least one selected from the group consisting of a virtual reality environment, an augmented reality environment, and a mixed-reality environment.

10. A computer system comprising:

a memory; and a processor in communication with the memory, wherein the computer system is configured to perform a method comprising:

maintaining user-specific parameters for provision of sensory feedback to a user in extended reality, the user-specific parameters applying to specific contextual situations and dictating levels of sensory feedback to provide via one or more stimulus devices in the specific contextual situations, wherein the maintaining comprises using feedback captured from user responses to generated prompts to the user, as input to train a Multi-Agent Reinforcement Learning (MARL) artificial intelligence (AI) model to identify the user-specific parameters applying to the specific contextual situations;

based on an ascertained contextual situation of the user interacting in a target extended reality environment, selecting a set of sensory feedback level parameters for provision of sensory feedback to the user in the target extended reality environment, wherein the sensory feedback is in response to generating a plurality of questions about a user's comfort level, wherein the selecting comprises applying the MARL AI model to features of the ascertained contextual situation and obtaining as an output of the MARL AI model a classification of the set of sensory feedback level parameters, wherein the sensory feedback is personalized to the user based on employing a reward function parametrized on factors including sentiment data and accelerometer data, wherein the sentiment data is detected by an NLP engine and the accelerometer data including the user's movement and orientation in space is captured with an accelerometer;

training the MARL AI model in real-time using the sensory feedback from a user apparatus producing the accelerometer data, the sensory feedback being received from the user in real-time including new reactions, iteratively adjusting the set of sensory feedback level parameters of the MARL AI model based on the sensory feedback; and automatically controlling, in the provision of the sensory feedback to the user in the target extended reality environment, at least one stimulus device in the target extended reality environment based on one or more of the selected parameters, the automatically controlling comprising electronically communicating with the at least one stimulus device to control one or more stimuli provided to the user by the at least one stimulus device.

11. The computer system of claim 10, wherein the maintaining the user-specific parameters comprises maintaining unique sets of sensory feedback level parameters correlating to different contextual situations in which user reactions have been previously observed.

12. The computer system of claim 11, wherein the selecting comprises comparing the ascertained contextual situation to one or more of the different contextual situations and determining based on the comparing whether the ascertained contextual situation corresponds to a contextual situation of the different contextual situations, and wherein the selecting of the selected set of sensory feedback level parameters is based on the determining.

13. The computer system of claim 12, wherein the determining determines that the ascertained contextual situation corresponds to a contextual situation of the different contextual situations, and wherein the selected set of sensory feedback level parameters is the unique set of sensory feedback level parameters correlating to the contextual situation to which the ascertained contextual situation corresponds.

14. The computer system of claim 12, wherein maintaining the user-specific parameters comprises maintaining one or more sets of anticipated preferred sensory feedback levels for the user, wherein the determining determines that the ascertained contextual situation does not correspond to any contextual situation of the different contextual situations, and wherein the selected set of sensory feedback level parameters is a set of anticipated preferred sensory feedback level parameters of the one or more sets of anticipated preferred sensory feedback levels for the user.

15. The computer system of claim 14, wherein the selected set of anticipated preferred sensory feedback level parameters for the user is based on a template set of sensory feedback level parameters built based on a population of users in which the user is classified.

16. The computer system of claim 10, wherein the maintaining further comprises employing observed user reactions to provided stimuli in one or more extended reality environments.

17. A computer program product comprising:

a computer readable storage medium readable by a processing circuit and storing instructions for execution by the processing circuit for performing a method comprising:

maintaining user-specific parameters for provision of sensory feedback to a user in extended reality, the user-specific parameters applying to specific contextual situations and dictating levels of sensory feedback to provide via one or more stimulus devices in the specific contextual situations, wherein the maintaining comprises using feedback captured from user responses to generated prompts to the user, as input to train a Multi-Agent Reinforcement Learning (MARL) artificial intelligence (AI) model to identify the user-specific parameters applying to the specific contextual situations;

based on an ascertained contextual situation of the user interacting in a target extended reality environment, selecting a set of sensory feedback level parameters for provision of sensory feedback to the user in the target extended reality environment, wherein the sensory feedback is in response to generating a plurality of questions about a user's comfort level, wherein the selecting comprises applying the MARL AI model to features of the ascertained contextual situation and obtaining as an output of the MARL AI model a classification of the set of sensory feedback level parameters, wherein the sensory feedback is personalized to the user based on employing a reward function parametrized on factors including sentiment data and accelerometer data, wherein the sentiment data is detected by an NLP engine and the accelerometer data including the user's movement and orientation in space is captured with an accelerometer;

training the MARL AI model in real-time using the sensory feedback from a user apparatus producing the accelerometer data, the sensory feedback being received from the user in real-time including new reactions, iteratively adjusting the set of sensory feedback level parameters of the MARL AI model based on the sensory feedback; and automatically controlling, in the provision of the sensory feedback to the user in the target extended reality environment, at least one stimulus device in the target extended reality environment based on one or more of the selected parameters, the automatically controlling comprising electronically communicating with the at least one stimulus device to control one or more stimuli provided to the user by the at least one stimulus device.

18. The computer program product of claim 17, wherein the maintaining the user-specific parameters comprises maintaining unique sets of sensory feedback level parameters correlating to different contextual situations in which user reactions have been previously observed, wherein the selecting comprises comparing the ascertained contextual situation to one or more of the different contextual situations and determining based on the comparing whether the ascertained contextual situation corresponds to a contextual situation of the different contextual situations, and wherein the selecting of the selected set of sensory feedback level parameters is based on the determining.

19. The computer program product of claim 18, wherein the determining determines that the ascertained contextual situation corresponds to a contextual situation of the different contextual situations, and wherein the selected set of sensory feedback level parameters is the unique set of sensory feedback level parameters correlating to the contextual situation to which the ascertained contextual situation corresponds.

20. The computer program product of claim 18, wherein maintaining the user-specific parameters comprises maintaining one or more sets of anticipated preferred sensory feedback levels for the user, wherein the determining determines that the ascertained contextual situation does not correspond to any contextual situation of the different contextual situations, wherein the selected set of sensory feedback level parameters is a set of anticipated preferred sensory feedback level parameters of the one or more sets of anticipated preferred sensory feedback levels for the user, and wherein the selected set of anticipated preferred sensory feedback level parameters for the user is based on a template set of sensory feedback level parameters built based on a population of users in which the user is classified.

* * * * *